United States Patent [19]
Van Scott et al.

[11] 3,932,665
[45] Jan. 13, 1976

[54] PROCESS FOR THE TREATMENT OF ACNE VULGARIS UTILIZING RETINAL

[76] Inventors: Eugene J. Van Scott, 1138 Sewell Lane, Rydal, Pa. 19046; Ruey J. Yu, 4400 Dexter St., Philadelphia, Pa. 19128

[22] Filed: Apr. 5, 1974

[21] Appl. No.: 458,095

[52] U.S. Cl. ............................... 424/333; 424/318
[51] Int. Cl.² ........................ 424 344; A61K 31/11
[58] Field of Search ................. 424/333, 318, 344

[56] References Cited
UNITED STATES PATENTS
3,729,568   4/1973   Kligman .................... 424/344 X FOREIGN PATENTS OR APPLICATIONS
901,659   7/1962   United Kingdom ............ 424/344

*Primary Examiner*—Norman A. Drezin
*Attorney, Agent, or Firm*—Myron B. Sokolowski

[57] ABSTRACT

This invention involves the use of retinal in topical therapy of acne vulgaris.

3 Claims, No Drawings

PROCESS FOR THE TREATMENT OF ACNE VULGARIS UTILIZING RETINAL

BACKGROUND OF THE INVENTION

1. Field of the Invention

Acne vulgaris (hereafter referred to as "acne") is a dermatological disorder which commonly affects pre-adolescents, adolescents, and young adults. The principal clinical manifestation of the disease is the occurrence of numerous cutaneous lesions which involve the pilosebaceous follicles on the face, shoulders, chest or back. While there are a variety of lesions such as comedones, papules, pustules, and cysts associated with acne, the primary and predominant lesion which affects the pilosebaceous follicle is the comedo.

The etiology of acne is yet unknown, although some aspects of the pathogenesis of the disease, specifically the formation of comedones, have been clarified. The normal pilosebaceous follicle includes a follicular canal which is open at one end to the surface of the skin through a follicular orifice and which terminates at its other end in a cul de sac in the dermal layer of the skin. At the base of such cul de sac is a vellus hair follicle. Surrounding the neck and the cul de sac end of the follicular canal are one or more multiacinar holocrine sebaceous glands which connect with the lumen of the follicular canal by means of glandular ducts. The acini of the glands have a peripheral layer of highly proliferating undifferentiated basal cells. As these basal cells are displaced from the periphery to the center of the acini by the proliferation of other basal cells, they mature and differentiate into lipid-producing cells. These cells continue to produce a variety of lipids and to store such lipids in their cytoplasm until they eventually rupture. The lipid contents and the cellular debris of such cells forms the secretion of the sebaceous glands known as sebum. In the normal state, the sebum is expelled through the glandular ducts and the follicular canal to the surface of the skin. In acne, the normal function of the pilosebaceous follicle is disrupted by an unexplained accumulation of lipid and keratinous material in the middle of the follicular canal, which accumulation ultimately becomes a comedo. As more lipid and keratinous material are deposited on the comedo, the follicular canal begins to distend and the sebaceous glands start to atrophy. Eventually the sebaceous glands are replaced by undifferentiated epithelial cells which surround the comedo. If the comedo is exposed to the surface of the skin and involves the follicular orifice, it is classified as "open"; otherwise, it is referred to as "closed". Open comedones generally are not inflammatory while closed comedones may evolve into inflamed pustules, papules, or cysts.

Therapeutic regimens for acne involve local and systemic therapies, although the former is indicated in the vast majority of cases. Closed comedones generally are excised by local surgery. Open comedones, on the other hand, currently are treated by topical application of a variety of chemical agents which include, in the main, sulfur, resorcinol, salicylic acid, benzoyl peroxide, Vleminckx's solution (comprising sulfur, calcium polysulfide, and calcium thiosulfate), or retinoic acid (vitamin A acid). All the foregoing topical agents are known as "peeling" or "drying" agents which are believed to exert their therapeutic effect by causing erythema, irritation, and desquamation of the skin to expel comedones. The therapeutic efficacy of these agents, however, is rather variable, and their utility is limited because of the irritation caused by their application.

For further details pertaining to the field, the following review article is recommended — J. S. Strauss, "Diseases of Sebaceous Glands", in: *Dermatology in General Medicine*, T. B. Fitzpatrick et al., Editors, New York, McGraw-Hill and Co., 1971, pp. 353–375.

2. Description of the Prior Art

M. T. Maynard (Arch. Dermatol. Syphilo., 42: 846 [1941]) and J. V. Straumford (Northwest Med., 42: 219 [1943]) have reported a systemic regimen for the treatment of acne which involves oral large doses of retinol (also known as vitamin $A_1$ or axerophthol) over a prolonged period of time. The results reported by Maynard and Straumford, however, have been disputed and the efficacy of systemic therapy of acne utilizing retinol has been challenged by other investigators: J. A. Anderson et al. (Brit. Med. J., 2: 294 [1963]); F. W. Lynch et al. (Arch. Derm., 55: 355 [1947]); and G. H. Mitchell et al. (Arch. Derm., 64: 428 [1951]).

Oral administration of retinol, however, appears to have effectiveness in the management of certain hyperkeratotic skin diseases such as Darier's disease (Z. A. Leitner et al., Lancet, 251: 262 [1946]), Devergie's disease (A. L. Weiner et al., Arch. Dermatol. Syphilol., 48: 288 [1943]), and ichthyosis (J. P. Fisher, Arch. Dermatol. Syphilol., 199: 459 [1955]).

Successful topical treatment of psoriasis and ichthyosis utilizing retinoic acid (also known as vitamin A acid) has been reported by P. Von Beer (Dermatologica, 124: 192 [1962]), C. Stuttgen (Dermatologica, 124: 65 [1962]), and P. Frost et al. (Clin. Res., 16: 255 [1965]). Although Von Beer and Stuttgen attempted topical treatment of acne utilizing retinoic acid, the results were equivocal.

A. M. Kligman et al. (Arch. Derm., 99: 469 [1969]) have demonstrated effective topical treatment of open and closed comedones associated with acne by use of 0.1% solutions of retinoic acid. Kligman et al. attribute the effectiveness of the retinoic acid to its irritating properties and hence its "peeling" ability. See also the disclosure by A. M. Kligman in U.S. Pat. No. 3,729,568 (Apr. 24, 1973).

Cosmetic compositions comprising retinoic acid or esters thereof together with other ingredients are described in British Pat. No. 906,000 (Sept. 19, 1962). These compositions are not intended for the treatment of acne but rather for cosmetic control of normal keratinization of the skin which may occur after exposure to unfavorable climatic conditions.

Compositions containing resorcinol, vitamin A or its derivatives and a polyalkylene glycol for use in the treatment of acne are disclosed in British Pat. No. 901,659 (July 25, 1962). According to the specification of this patent, the resorcinol prevents the worsening of the acne by vitamin A (or its derivatives) during the early stages of therapy and the polyalkylene glycol prevents the irritation caused by the resorcinol.

SUMMARY OF THE INVENTION

The subject matter of this invention is a therapeutic method of treating acne vulgaris (acne) in humans by administering to areas of skin affected by acne an effective amount of retinal. The unexpected result of this invention is that retinal, unlike retinoic acid, exerts its therapeutic effects without producing irritation, inflammation, erythema or peeling of the skin. Retinal is as effective, however, as retinoic acid in its ability to clear affected skin of open and closed comedones.

Compositions comprising retinal in therapeutically effective amounts and pharmacologically acceptable vehicles which are nonirritating to the skin are convenient for the administration of the retinal.

Retinal has been found to be effective in from about 0.05 to about 1% by weight relative to the vehicle. Although amounts greater than 1% by weight may be safely used without causing irritation, the efficacy of treatment is not increased. Generally, however, amounts from about 0.1 to about 0.2% by weight will provide the desired therapeutic effect and are preferred.

Suitable vehicles for the administration of the retinal can be liquids, cremes, or ointments.

Convenient liquid vehicles which are useful in the application of retinal to areas of skin affected by acne include: water; alcohols such as methanol, ethanol, propanol, and isopropanol; water-alcohol solutions; or water-alcohol-polyalkyleneglycol solutions. Ethanol (95%) is a preferred alcoholic vehicle and propylene glycol is a preferred vehicle of the polyalkylene glycol class. A convenient vehicle for the administration of retinal is a water-ethanol-propylene glycol solution having a weight composition of 50% water, 30% ethanol, and 20% propylene glycol.

Convenient vehicles which are ointments or cremes include: Hydrophilic Ointment, U.S.P., and ACID MANTLE creme. The formulation of Hydrophilic Ointment, U.S.P. is well known and is reported in the following references: *Drugs of Choice*, 1972–1973, W. Modell, Ed., St. Louis, C. V. Mosby Co., p. 677 (1972); *The Pharmacopeia of the United States*, 17th Edition, Easton, Mack Publishing Co., pages 422 and 448. ACID MANTLE creme is commercially available from the Dome Division of Miles Laboratories, Inc., West Haven, Connecticut and is reported in the following reference: *Physicians' Desk Reference to Pharmaceutical Specialties and Biologics*, B. Huff, Ed., Oradell, N.J., Medical Economics Co., p. 704 (1973). ACID MANTLE is hydrophilic ointment, U.S.P., containing from about 0.5% to about 1% of aluminum acetate by weight.

Retinal (also known as retinene, vitamin A aldehyde, or axerophthal) has an empirical formula of $C_{20}H_{28}O$ and a molecular weight of 284.42. Structurally, retinal may exist in four (4) stereoisomeric forms.

1. All-<u>trans</u>,

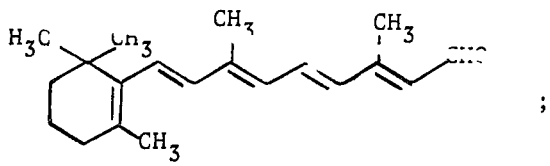

;

2. 13-<u>cis</u>,

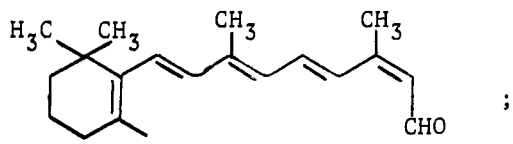

;

3. 11-<u>cis</u>,

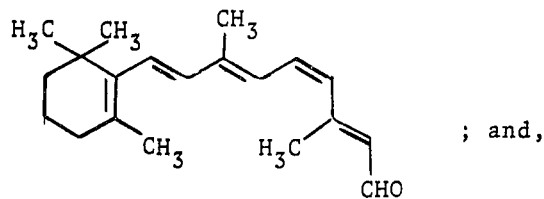

; and, 4. 9-<u>cis</u>,

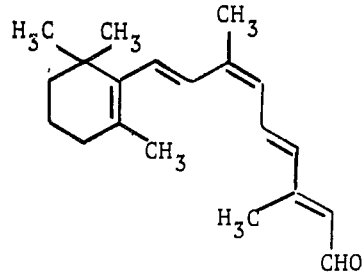

All four of the above stereoisomers exhibit biological activity as vitamins relative to retinol and all are useful in the topical treatment of acne. It is emphasized, however, that the latter use of retinal is not dependent upon its physiological properties as a vitamin.

Retinal can be prepared by oxidation of retinol (S. Ball et al., Biochem. J., 42: 516 [1948]) or from β-ionene (K. Eiter et al., U.S. Pat. No. 3,060,299; Oct. 23, 1973).

For a comprehensive review of the chemical properties, synthesis, and biological activity of retinal, see — R. S. Harris, et al., "Vitamins A and Carotene" in: *The Vitamins*, Volume I, W. H. Sebrell, Jr. et al., Editors, New York, Academic Press, 1967, Chapter 1.

DESCRIPTION OF THE PREFERRED EMBODIMENTS

Example 1

The skin of the rhino mouse, a mutant strain of the hairless mouse (P. D. Forbes, J. Invest. Derm., 44: 388 [1965]) develops spontaneous comedones in its philosebaceous follicles (S. Mann, Anat. Rec., 170: 485 [1971]) and is a model system for the pharmacologic testing of agents for the treatment of acne (E. J. Van Scott, "Experimental Animal Integumental Models for Screening Potential Dermatologic Drugs," in: *Advances in Biology of the Skin: Vol. XII, Pharmacology and the Skin*, W. Montagna et al., Editors New York, Meredith Corp., 1972, Chapter XXXIII).

For purposes of comparing, retinol, retinol palmitate, retinal and retinoic acid were applied to the skin of rhino mice in solutions of water-ethanol-propylene glycol (5:3:2) at concentrations ranging from 0.05 to 1% by weight for a period of from 1 to 3 weeks. The effects of these agents were determined macroscopically and histologically at weekly intervals. Observations were made regarding the irritation caused by the various agents to the skin, specifically the presence of erythema, inflammation, and desquamation of the skin.

The results of these experiments are presented in Table I. As can be seen from Table I, neither retinol nor retinol palmitate eliminated comedones in the rhino mouse under the conditions of the experiment. Both all -trans and 13-cis retinal were as effective as retinoic acid in the treatment of comedones and did not cause irritation to the skin which accompanied retinoic acid treatment. Administration of the water-ethanol-propylene glycol vehicle to control animals produced no effect on the comedones nor did it cause irritation.

Table II presents comparative data relating to the absence or presence of irritation observed upon topical application of the various vitamin A analogues on the normal skin of another test animal, in this case the ICR (Institute for Cancer Research) Mouse. While retinoic acid and retinol palmitate caused irritation, retinal and retinol did not.

TABLE I

Effects of Topically Applied Vitamin A Analogues[a] on the Skin of the Rhino Mouse

| Compound* | Concentration % | Period of topical application[b] | Effect on comedones[c] | Number of granular layers | Thickness of epidermis | Irritancy to skin |
|---|---|---|---|---|---|---|
| Retinol (Vitamin A Alcohol) | 0.05 | 1 wk | 0 | 0–1 | 20–30μ | |
|  | 0.1 | 2 wks | ++ | 2–4 | 30–50μ | no |
|  | 0.5 | 1 wk | +++ | 2–3 | 30–50μ | |
| Retinol Palmitate | 0.05 | 3 wks | + | 3 | 20–30μ | |
|  | 0.2 | 1 wk | ++ | 2–3 | 20–50μ | no |
|  | 1.0 | 1 wk | +++ | 2–3 | 20–50μ | |
| Retinal (Vitamin A Aldehyde) | 0.05 | 1 wk | +++ | 3–4 | 20–50μ | |
|  | 0.05 | 2 wks | ++++ | 2–4 | 30–70μ | no |
|  | 0.1 | 1 wk | ++++ | 0–1 | 30–70μ | |
|  | 0.5 | 1 wk | ++ ++ | 0 | 30–50μ | |
| Retinal (13-cis) | 0.1 | 2 wks | ++++ | 3–5 | 30–50μ | no |
| Retinoic Acid (Vitamin A Acid) | 0.05 | 1 wk | ++++ | 0 | 20–30μ | yes |
|  | 0.05 | 2 wks | ++++ | 0 | 20–30μ | |
| Vehicle[d] |  | 1 wk | 0 |  |  | no |
|  |  | 3 wks | 0 |  |  | |

[a] All in trans form except as indicated.
[b] Topical application 2× daily.
[c] 0, No difference from controls, comedones extending into follicular orifice to depth of 150–200μ:
+, comedones extending into follicular orifice to depth of 100–150μ
++, comedones extending into follicular orifice to depth of 50–100μ
+++, comedones present, extending into follicular orifice to depth of 1–50μ
++++, epidermis "normal", devoid of comedones.
[d] Water-Ethanol-Propylene Glycol (5:3:2).
*Each compound tested on five (5) animals.

TABLE II

Effects of Topically Applied Vitamin A Analogues[a] on the Skin of the ICR Mouse[b]

| Compound* | Concentration % | Number of granular layers | Thickness of stratum corneum | Thickness of epidermis | Irritancy to skin |
|---|---|---|---|---|---|
| Retinol (Vitamin A Alcohol) | 0.5 | 4 | 10μ | 30–80μ | no |
| Retinol Palmitate | 1.0 | 2–4 | 10–30μ | 20–70μ | yes |
| Retinal (Vitamin A Aldehyde) | 0.05 | 3–4 | 10μ, compact | 30–50μ | no |
| Retinoic Acid (Vitamin A Acid) | 0.05 | 4–6 | 10μ, compact | 30–70μ | yes |

TABLE II-continued

Effects of Topically Applied Vitamin A Analogues[a] on the Skin of the ICR Mouse[b]

| Compound* | Concentration % | Number of granular layers | Thickness of stratum corneum | Thickness of epidermis | Irritancy to skin |
|---|---|---|---|---|---|
| Controls[c] | | 1 | 10–20μ | | |

[a] All in trans form.
[b] Topical application 1× daily for 1 week.
[c] Untreated animals; vehicle treated animals: water-ethanol-propylene glycol (5:3:2).
*Each compound tested on ten (10) animals.

Example 2

This Example compares therapeutic effectiveness of topically applied retinal (vitamin A aldehyde) and retinol acetate (acetate ester of vitamin A alcohol) with the effectiveness of vehicle alone (water-ethanol-propylene glycol: 5:3:2) in human subjects. The retinal and retinol acetate, purchased as pure chemicals, were dissolved in 0.1% concentration in water-ethanol-propylene glycol (5:3:2). The two test materials and vehicle alone were put in separate 2 oz. amber bottles, and labeled according to code numbers. Thirty-nine patient volunteers were recruited from a high school population and were randomly assigned to each of three groups. Each group consisted of 12–14 subjects, of whom approximately half were boys and half were girls. The subjects were selected on the basis of their having moderate to severe papular-pustular acne. Parental consent to participate in the study was obtained by signature of a consent document which included full explanation of the study. No other acne treatment nor the use of cosmetics was permitted during the study period. The study was carried out in a double-blind, randomized fashion. Neither the patient nor physician knew the identity of the preparation used. Standardized color photos for projection were taken of the full face and each side of the face at times 0 (the day the study is initiated), at 4 weeks and at 8 weeks. Preparations were applied to the face in the morning and evening after washing the face with ordinary soap. Patients were observed at times 0, 1 week, 4 weeks and 8 weeks to assure that treatments were carried out according to directions. Prior experience comparing means to evaluate treatment results in acne has shown that photographic records are the most reliable, and that physician clinical impressions without reference photographic records or patient impressions to be totally unreliable. Therefore, each subject's response was measured from photos projected at standard distance. Judgments of "improvement," "no change," or "worse" were made by a panel of three dermatologists who had no knowledge of the preparation used by each patient; projection of photos was randomized from case to case so that the sequence of "before," "during," and "after" treatment photos was varied. The code of the preparations was broken only after evaluation was completed.

Results of this study are presented in Tables III and IV. The data indicate that retinal had effectiveness in the treatment of acne in at least 50% of the subjects treated with retinal. It is important to note that in all subjects receiving retinal therapy no irritation of the skin was observed.

In a separate half-face comparison study to determine the irritation caused by retinal and retinoic acid in six human volunteers, retinal was applied on one cheek while retinoic acid was applied on the other. In all six cases there was macroscopic irritation of the cheek treated with the acid and no irritation of the cheek treated with the aldehyde.

TABLE III

ACNE STUDY FACE
PHOTOGRAPHIC EVALUATION 0 AND 4 WEEKS

| GROUP NO. | WORSE | NO CHANGE | BETTER |
|---|---|---|---|
| No. 1 Vehicle | 2 | 8 | 2 |
| No. 2 Retinal | 4 | 3 | 7 |
| No. 3 Retinol Acetate | 1 | 9 | 3 |
| TOTALS TOTAL 39 | 7 | 20 | 12 |

TABLE IV

ACNE STUDY FACE
PHOTOGRAPHIC EVALUATION 0 AND 8 WEEKS

| GROUP NO. | WORSE | NO CHANGE | BETTER |
|---|---|---|---|
| No. 1 Vehicle | | 9 | 3 |
| No. 2 Retinal | 1 | 6 | 7 |
| No. 3 Retinol Acetate | 3 | 8 | 2 |
| TOTALS TOTAL 39 | 4 | 23 | 12 |

What is claimed is:

1. A method of treating acne vulgaris in a human having skin affected thereby, which method consists of: administering topically to the affected skin a therapeutically effective amount of retinal on a daily basis to promote improvement of the skin without causing worsening of the acne, irritation to the skin, and peeling of the skin.

2. A method as in claim 1, wherein the retinal is administered in an amount of from about 0.05 to about 1% by weight in a pharmacologically acceptable topical vehicle.

3. A method as in claim 2, wherein the retinal is in an amount of from about 0.1 to 0.2% by weight.

* * * * *